United States Patent [19]

Stark, Jr.

[11] Plant 4,731

[45] Jun. 2, 1981

[54] APPLE TREE-GOLDENSHEEN #2 CULTIVAR

[75] Inventor: Paul C. Stark, Jr., Louisiana, Mo.

[73] Assignee: Stark Brothers Nurseries & Orchards Co., Louisiana, Mo.

[21] Appl. No.: 115,546

[22] Filed: Jan. 25, 1980

[51] Int. Cl.[3] ..... A01H 5/00

[52] U.S. Cl. ..... Plt./34

[58] Field of Search ..... Plt./34

*Primary Examiner*—James R. Feyrer

*Attorney, Agent, or Firm*—Burns, Doane, Swecker & Mathis

[57] ABSTRACT

The new variety is a whole tree mutation of the Goldensheen apple tree (French Brevet D'Invention 70.47735) which was discovered at Louisiana, Mo. The new variety produces attractive solid yellow apples as does the parent Goldensheen variety which are unusually free and resistant to the russeting commonly observed on apples of the Golden Delicious type. Unlike the Goldensheen parent the new variety is a larger standard bearing tree having a vigorous and spreading growth habit instead of possessing a compact spur fruit-bearing habit.

2 Drawing Figures

SUMMARY OF THE INVENTION

The present invention relates to a new and distinct variety of apple tree which was discovered by me as a whole tree mutation of the Goldensheen cultivar (French Brevet D'Invention No. 70.47735) growing in the Test Orchard of Stark Brothers Nurseries and Orchards Company at Louisiana, Pike County, Mo.

My attention was first directed to what is now considered to be the new variety while I was engaged in making a routine orchard inspection of Goldensheen cultivar research plantings and comparing the growth habit exhibited with that of the Golden Delicious — Mullins cultivar (not patented) which has been marketed by the Stark Brothers Orchards and Nurseries Company for a number of years. The Goldensheen cultivar specimens undergoing observation had been obtained for test purposes from the Pepinieres et Roseraies Georges Delbard of France.

As described in the French Brevet D'Invention, the Goldensheen cultivar is a compact spur-type tree which is a semi-dwarf of no more than approximately 75 percent the size of a standard non-spur apple variety, such as the Golden Delicious-Mullins cultivar (not patented), growing on a similar rootstock. Additionally, the Goldensheen cultivar unlike the Golden Delicious-Mullins cultivar has been recognized to form fruit which is unusually free and resistant to russeting. The term "russeting" is used herein to designate defects appearing on the fruit skin such as bronzing, roughness, and corky spots. Such defects can be present as small dots or as a larger network which covers a part or all of the fruit surface. The russeting commonly is believed to be a defensive reaction of the epidermic and the cuticle tissue to external and internal causes unfavorable to the normal development of the skin such as cold or wet weather during the post-blossom season, or abrasive chemicals used for insect or disease control.

Further observations of the new variety which extended over a number of years confirmed its new and distinctive characteristics. More specifically, the same attractive fruit characteristics of the Goldensheen cultivar wherein the fruit was unusually free and resistant to russeting were exihibited by the new variety. However, the tree exhibited a very vigorous and spreading growing form similar to that of the Golden Delicious —

Mullins cultivar, and was a standard sized tree rather than a compact spur-type tree as the Goldensheen cultivar. The fruit of the new variety was borne on the terminal portion of two and three year old shoots rather than on spurs as was characteristic of the Goldensheen cultivar. Also, the new variety was found to mature later and to form smaller flowers than the Golden Delicious — Mullins cultivar.

This new variety of apple tree was found to possess the following combination of characteristics:

(a) upon maturity is a medium-large vigorous tree with an open and spreading growth habit, (b) forms medium-large parsley green leaves, (c) forms small white flowers which are late blooming in comparison to other varieties, (d) forms attractive large, typey and round conic fruit with a deep Dresden yellow skin color which is substantially free of russeting, and (e) possesses a bearing habit whereby fruit buds are borne on the terminal portions of two and three year old shoots annually and regularly.

Asexual propagation over a number of years has demonstrated that the unique characteristics of this new variety come true-to-form and are established and transmitted through succeeding propagations. The new variety has been named the Goldensheen #2 cultivar.

BRIEF DESCRIPTION OF THE PHOTOGRAPHS

DETAILED DESCRIPTION

Figure 1:
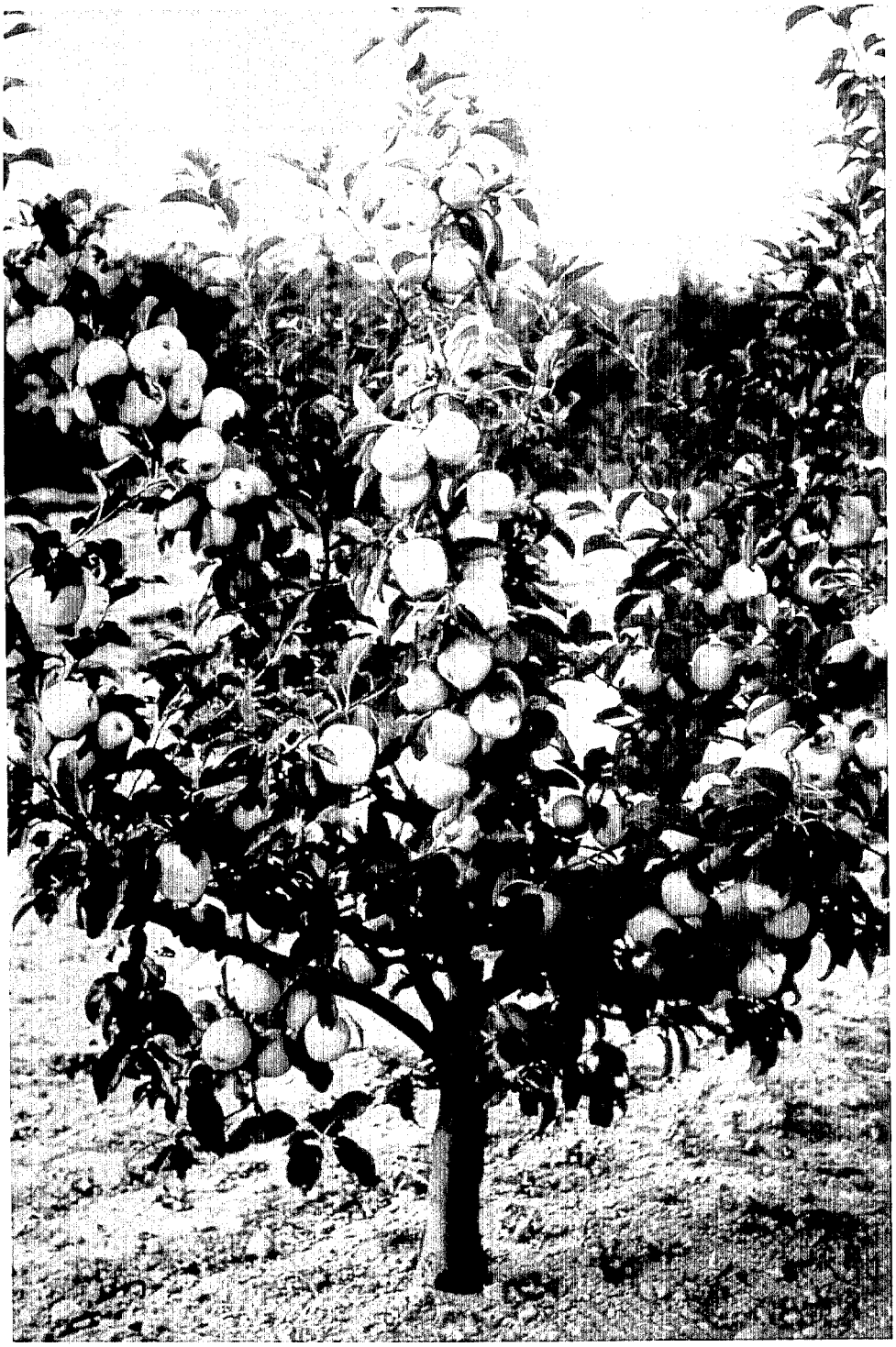
FIG. 1 shows in color as true as is reasonably possible a typical tree of the previously known Goldensheen cultivar of approximately 10 years of age growing at Louisiana, Mo. The compact spur fruit-bearing habit is apparent.
Figure 2:
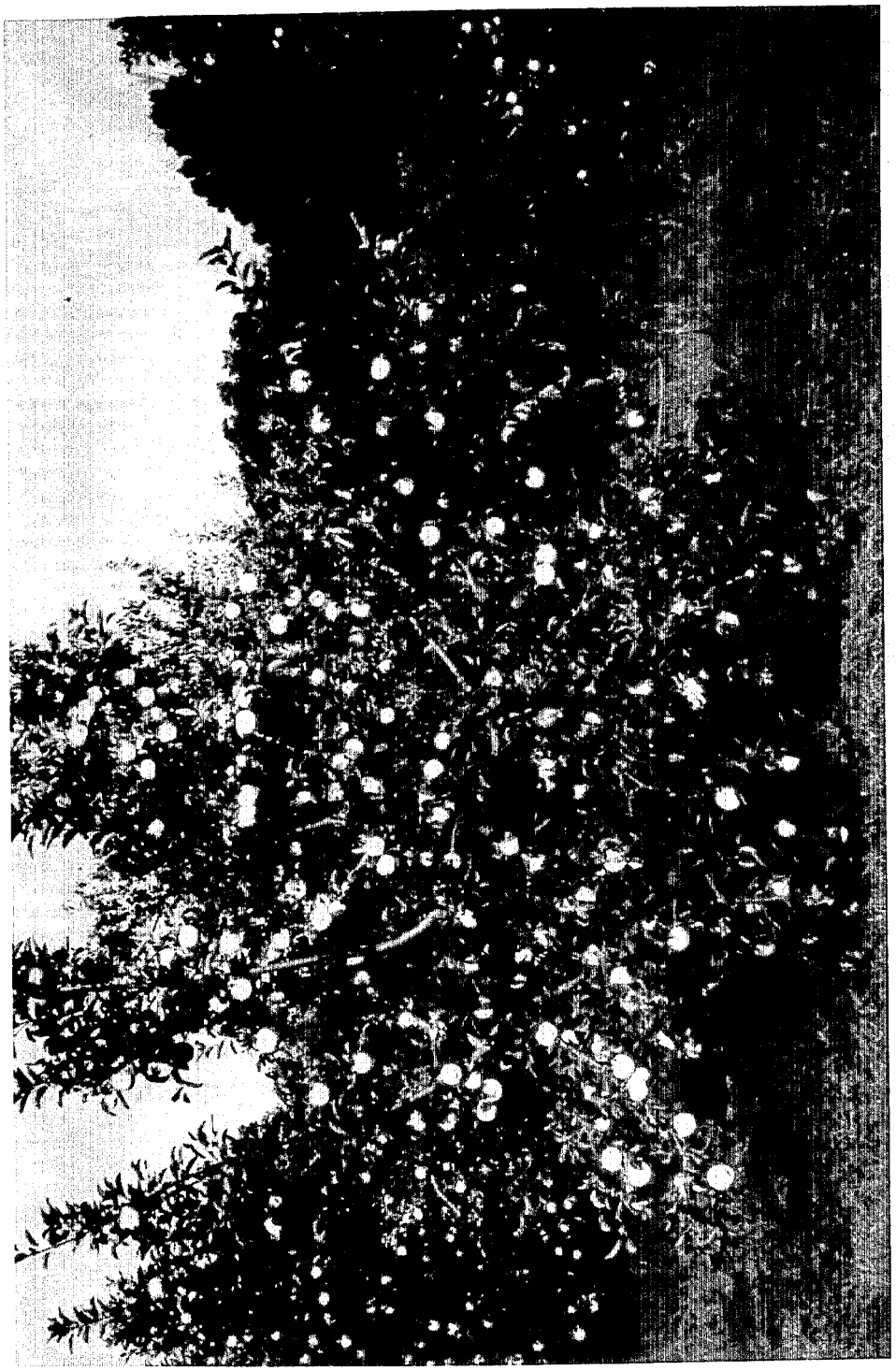
FIG. 2 shows in color as true as is reasonably possible a typical tree of the presently claimed Goldensheen #2 cultivar of approximately 10 years of age growing at Louisiana, Mo. The larger spreading growth habit of the new variety is apparent.

The following is a detailed description of my new variety where color terminology is to be accorded its ordinary dictionary significance except where otherwise indicated. The specimens described were grown at Louisiana, Mo.

Dates first and last picking — Oct. 20 and Oct. 29, 1979.

Tree: Medium large; vigorous; spreading; tall; open; rapid growing; hardy; very productive; regular bearing.

*Trunk.*—Stocky; smooth.

*Branches.*—Thick; smooth; color — Light Tropical Olive — Plate XLVI Color #21 tone "B" of Ridgeway Color Standards.

*Leaves.*—Length — approximately 4 inches; width — approximately 2¼ inches; medium large; medium wide; medium long; oval; abruptly pointed; medium thick; color — Parsley green color #009621 — Pg. 193 — Vol. II of Horticultural Color Guide.

*Margin.*—Coarsely serrate.

*Petiole.*—Medium short; medium thick.

Flowers: Date of first bloom — Apr. 20, 1979; date of full bloom — Apr. 25, 1979; late; small; white with pink tinge.

Fruit: Maturity when eating ripe — Oct. 20, 1979.

*Size.*—Uniform; axial diameter — approximately 3½ to 4 inches; transverse diameter — approximately 3 to 4 inches; trunate at base; very typey; conical.

*Cavity.*—Symmetrical; rounded at base; apex — acute; undulate; crowned; depth — approximately ¾ inch; breadth — approximately 1⅛ inch.

*Basin.*—Symmetrical; abrupt at base; wide base; undulate; crowned; glabrous; depth — approximately ⅜ inch; breadth — approximately 1⅛ inch; markings — none.

*Stem.*—Medium slender; pubescent; length — approximately ¾ inch; breadth — approximately 1⅛ inch; markings — none.

*Calyx.*—Open. Segments — Persistent; acute; length — approximately 3/16 inch; separated; reflexed from base at apex; outer surface — pubescent; inner surface — pubescent.

*Eye.*—Large; open.

*Skin.*—Thin; tender; smooth; waxed. Dots — Conspicuous; many; small; raised; circular. Color of Dots — Brown. Distribution of Dots — Over entire surface. Ground Color — Yellow, Dresden Yellow 6/2 pg. 64, vol. I of Horticultural Color Guide. Color markings — Blushed with full sun exposure — Munsell strong pink 2, 5R 718, to deep pink 2, 5R/6/11. Bloom — Wanting. General color effect — Golden yellow as parent Goldensheen cultivar.

*Flesh.*—Juicy. Color of flesh — White with yellowish tint. Texture — Firm; fine. Flavor — Subacid; mild; rich. Aroma — Distinct. Quality — Best.

*Core.*—Median. Bundle area (longitudinal section) — Medium small; cordate; symmetrical; acute at base. Halves of area — Equal. Bundles — Yellowish; inconspicuous; in two whorls. Alternate Bundle — Core lines — meeting; carpellary area distinct; small. Calyx-tube — Glabrous toward base; cone shaped; entire depth — approximately ½ inch. Styles — Present; united toward base. Stamens — In one whorl; median. Auxillary cavity — Wanting.

*Seeds.*—Number perfect — 10; imperfect — 0. Number in one cell — 2. Length — Approximately ⅜ inch. Breadth — Approximately 3/16 inch. Form — Acute. Color — Brown — Mars Brown Plate XII — Color #13′ Tone 111 of Ridgeway Color Standards.

Use: Local Market; dessert; culinary; commercial market.

Keeping quality: Good — better than Golden Delicious — Mullins cultivar.

*Number of days in ordinary storage.*—Approximately 120 to 140+.

Resistance to:

*Insects.*—Medium.

*Diseases.*—Medium.

I claim:

1. A new and distinct variety of apple tree of the Golden Delicious type which is a whole tree mutation of the Goldensheen apple tree substantially as shown and described, characterized by (a) the ability to form fruit with a deep Dresden yellow skin which is unusually free and resistant to russeting substantially identical to that of the Goldensheen cultivar, (b) a vigorous and spreading growth habit which yields a standard sized tree unlike the Goldensheen cultivar, and (c) smaller flowers which appear later than those of the Golden Delicious — Mullins cultivar.

* * * * *